US012672910B2

(12) United States Patent
Williams et al.

(10) Patent No.: US 12,672,910 B2
(45) Date of Patent: * Jul. 7, 2026

(54) BIPOLAR ELECTROSURGICAL INSTRUMENTS

(71) Applicant: GYRUS ACMI, INC., Westborough, MA (US)

(72) Inventors: Wayne Williams, Penarth (GB); Lewis Jones, Cardiff (GB)

(73) Assignee: Gyrus ACMI, Inc., Westborough, MA (US)

( * ) Notice: Subject to any disclaimer, the term of this patent is extended or adjusted under 35 U.S.C. 154(b) by 63 days.

This patent is subject to a terminal disclaimer.

(21) Appl. No.: 18/369,388

(22) Filed: Sep. 18, 2023

(65) Prior Publication Data

US 2024/0000501 A1 Jan. 4, 2024

Related U.S. Application Data

(63) Continuation of application No. 16/438,693, filed on Jun. 12, 2019, now Pat. No. 11,786,293.

(30) Foreign Application Priority Data

Jun. 13, 2018 (GB) ...................................... 1809685

(51) Int. Cl.
A61B 18/12 (2006.01)
A61B 18/14 (2006.01)
(Continued)

(52) U.S. Cl.
CPC ...... *A61B 18/1445* (2013.01); *A61B 18/1206* (2013.01); *A61B 18/1442* (2013.01);
(Continued)

(58) Field of Classification Search
CPC ............ A61B 18/1206; A61B 18/1233; A61B 18/1445; A61B 2018/00589;
(Continued)

(56) References Cited

U.S. PATENT DOCUMENTS 5,540,684 A 7/1996 Hassler, Jr.
5,558,671 A 9/1996 Yates
(Continued)

OTHER PUBLICATIONS

Nov. 26, 2018 Search Report issued in European Patent Application No. GB1809685.9.
(Continued)

*Primary Examiner* — Daniel W Fowler
(74) *Attorney, Agent, or Firm* — Schwegman Lundberg & Woessner, P.A.

(57) ABSTRACT

A bipolar surgical instrument comprises a body first and second opposed jaws located at the distal end of a shaft, the first jaw being movable with respect to the second jaw between an open position in which the first and second jaws are spaced apart from one another, and a closed position in which the first and second jaws are adjacent one another. The first and second elongate jaw members have respective first and second electrodes. A controller is operable to determine a boiling point for tissue between the jaws using a measure of impedance therebetween.

8 Claims, 6 Drawing Sheets

(51) Int. Cl.
| | |
|---|---|
| *A61B 17/29* | (2006.01) |
| *A61B 18/00* | (2006.01) |

(52) U.S. Cl.
CPC ... *A61B 17/2909* (2013.01); *A61B 2018/0063* (2013.01); *A61B 2018/00642* (2013.01); *A61B 2018/00666* (2013.01); *A61B 2018/00672* (2013.01); *A61B 2018/00678* (2013.01); *A61B 2018/00702* (2013.01); *A61B 2018/00755* (2013.01); *A61B 2018/00761* (2013.01); *A61B 2018/00767* (2013.01); *A61B 2018/00827* (2013.01); *A61B 2018/00875* (2013.01); *A61B 2018/00892* (2013.01); *A61B 2018/126* (2013.01)

(58) Field of Classification Search
CPC ........... A61B 2018/00666; A61B 2018/00672; A61B 2018/00761; A61B 2018/00827; A61B 2018/00892; A61B 2018/00988; A61B 2018/126
See application file for complete search history.

(56) References Cited

U.S. PATENT DOCUMENTS

| | | | |
|---|---|---|---|
| 6,398,779 B1 | 6/2002 | Buysse et al. | |
| 2002/0091385 A1* | 7/2002 | Paton ................. | A61B 18/1442 606/51 |
| 2003/0158551 A1 | 8/2003 | Paton et al. | |
| 2004/0167508 A1* | 8/2004 | Wham ............... | A61B 18/1442 606/49 |
| 2005/0113817 A1* | 5/2005 | Isaacson ................ | A61B 18/16 606/34 |
| 2007/0173804 A1 | 7/2007 | Wham et al. | |
| 2008/0015575 A1 | 1/2008 | Odom et al. | |
| 2010/0042101 A1 | 2/2010 | Inagaki et al. | |
| 2011/0077630 A1 | 3/2011 | Tanaka et al. | |
| 2011/0306963 A1 | 12/2011 | Dietz et al. | |
| 2012/0101493 A1 | 4/2012 | Masuda et al. | |
| 2013/0296839 A1* | 11/2013 | Condie ............. | A61B 18/1206 606/33 |
| 2014/0025061 A1 | 1/2014 | Benamou | |
| 2014/0371735 A1 | 12/2014 | Long | |
| 2015/0374430 A1* | 12/2015 | Weiler ............... | A61B 18/1445 606/46 |
| 2016/0367308 A1 | 12/2016 | Takami et al. | |
| 2019/0380768 A1 | 12/2019 | Williams et al. | |

OTHER PUBLICATIONS

"U.S. Appl. No. 16/438,693, Final Office Action mailed Aug. 19, 2022", 13 pages.
"U.S. Appl. No. 16/438,693, Non Final Office Action mailed Jan. 28, 2022", 10 pgs.
"U.S. Appl. No. 16/438,693, Notice of Allowance mailed Jun. 14, 2023", 7 pgs.
"U.S. Appl. No. 16/438,693, Response filed Feb. 9, 2023 to Final Office Action mailed Aug. 19, 2022", 9 pgs.
"U.S. Appl. No. 16/438,693, Response filed Jul. 27, 2022 to Non Final Office Action mailed Jan. 28, 2022", 9 pgs.

\* cited by examiner

BIPOLAR ELECTROSURGICAL INSTRUMENTS

This application is a Continuation of U.S. patent application Ser. No. 16/438,693, filed Jun. 12, 2019, which in turn claims the benefit of Great Britain Patent Application No. 1809685.9, filed Jun. 13, 2018. The disclosure of the prior applications is hereby incorporated by reference herein in its entirety.

BACKGROUND OF THE INVENTION

The present invention relates to bipolar electrosurgical instruments.

Bipolar surgical instruments are used to clamp and seal tissue, such as blood vessels, during surgical procedures. Clamping is typically achieved using a pair of opposed jaws that are remotely operable to clamp around the vessel being sealed. Sealing is typically achieved using application of radio frequency energy delivered to the tissue being sealed by electrodes mounted on the opposed jaws of the instrument.

Existing designs of such instruments may not provide optimal transfer of electrical power to the tissue, and so may not provide optimal tissue sealing. For example, it is desirable to have acceptably short sealing times.

It is, therefore, desirable to provide an improved bipolar surgical instrument that, at least partially, addresses these drawbacks.

SUMMARY OF THE INVENTION

Aspects of the present invention are discussed below.

According to one exemplary aspect, there is provided an electrosurgical system comprising a bipolar electrosurgical instrument comprising a body; an elongate shaft attached to the body, the elongate shaft extending to a distal end; first and second elongate jaw members located at the distal end of the elongate shaft, and carrying respective first and second electrodes, the jaw members being movable relative to one another between an open position in which the first and second electrodes are spaced apart from one another, and a closed position in which the first electrode is adjacent the second electrode; and a power cable having a pair of electrically conductive elements, and having a first end for connection with a source of radio frequency electromagnetic energy, and a second end for connection to the first and second electrodes; and a waveform generator connected with the power cable of the bipolar electrosurgical instrument and comprising a radio frequency signal generator operable to supply a radio frequency signal to the first and second electrodes via the power cable; and a controller operable to control operation of the radio frequency signal generator, in dependence upon a received control input, wherein the controller is operable, in a heating stage to control the radio frequency generator to supply a radio frequency signal at a controlled voltage level to the first and second electrodes, the controlled voltage level starting at a starting voltage at a heating start time, and ending at a final voltage at a heating end time; to measure an impedance between the first and second electrodes during supply of the controlled voltage level; to detect a minimum measured impedance between the first and second electrodes; and to determine the heating end time as that time when the measured impedance is greater than the minimum impedance by a first predetermined amount.

In one example, the controller is operable, in an initialisation stage prior to the heating stage to control the radio frequency signal generator to supply a radio frequency signal of a predetermined initial power level to the first and second electrodes for a predetermined initial time period having an end time; to measure a voltage level between the first and second electrodes at the end time; and to store such a measured voltage as the starting voltage for the heating stage.

In one example, the controller is operable, in a sealing stage following the heating stage to supply a radio frequency signal at a predetermined sealing voltage level to the first and second electrodes for a predetermined sealing time period having a sealing end time; to measure an impedance level between the first and second electrodes at the sealing end time; to compare the measured impedance with a predetermined reference impedance to produce a comparison signal; and to determine a next mode of operation for the radio frequency signal generator in dependence upon such a comparison signal.

In such an example, the controller is operable, subsequent to the sealing stage, and when such a comparison signal is indicative of the measured impedance level being less than to the predetermined reference impedance level to repeat the heating and sealing stages until the comparison signal is indicative of the measured impedance level being greater than or equal to the predetermined reference impedance level.

In one example, the controller is operable, in a completion stage subsequent to the sealing stage, and when the comparison signal is indicative of the measured impedance level being greater than or equal to the predetermined reference impedance level to control the radio frequency signal generator to apply a radio frequency signal at a predetermined completion voltage level, lower than the predetermined sealing voltage level, for a predetermined completion time period; and to end supply of such radio frequency signals.

In one example, the controller is operable to measure electrical current supplied to the first and second electrodes to generate a measured current signal, and to detect a short circuit between the first and second electrodes if the measured current signal indicates electrical current supplied to the first and second electrodes exceeds a first predetermined value for at least a predetermined time period.

According to another exemplary example, there is provided a method of operating an electrosurgical system comprising a bipolar electrosurgical instrument comprising a body; an elongate shaft attached to the body, the elongate shaft extending to a distal end; first and second elongate jaw members located at the distal end of the elongate shaft, and carrying respective first and second electrodes, the jaw members being movable relative to one another between an open position in which the first and second electrodes are spaced apart from one another, and a closed position in which the first electrode is adjacent the second electrode; and a power cable having a pair of electrically conductive elements, and having a first end for connection with a source of radio frequency electromagnetic energy, and a second end for connection to the first and second electrodes; and a waveform generator connected with the power cable of the bipolar electrosurgical instrument and comprising a radio frequency signal generator operable to supply a radio frequency signal to the first and second electrodes via the power cable; and a controller operable to control operation of the radio frequency signal generator, in dependence upon a received control input, wherein the method comprises a heating stage comprising controlling the radio frequency generator to supply a radio frequency signal at a controlled voltage level to the first and second electrodes, the controlled voltage level starting at the starting voltage at an heating start time, and ending at a final voltage at an heating end time; measuring an impedance between the first and second electrodes during supply of the controlled voltage level; detecting a minimum measured impedance between the first and second electrodes; and determining the heating end time as that time when the measured impedance is greater than the minimum impedance by a first predetermined amount.

In one example, such a method further comprises, in advance of the heating stage, an initialisation stage comprising supplying a radio frequency signal of a predetermined initial power level to the first and second electrodes for a predetermined initial time period having an initialisation end time; measuring a voltage level between the first and second electrodes at the initialisation end time; and storing such a measured voltage as the starting voltage for the heating stage.

In one example, such a method further comprises, subsequent to the heating stage, a sealing stage comprising supplying a radio frequency signal at a predetermined sealing voltage level to the first and second electrodes for a predetermined sealing time period having a sealing end time; measuring an impedance level between the first and second electrodes at the sealing end time; comparing the measured impedance with a predetermined reference impedance to produce a comparison signal; and determining a next mode of operation for the radio frequency generator in dependence upon such a comparison signal.

In one example, such a method further comprises, subsequent to the sealing stage, and when such a comparison signal is indicative of the measured impedance level being less than to the predetermined reference impedance level repeating the heating and sealing stages until the comparison signal is indicative of the measured impedance level being greater than or equal to the predetermined reference impedance level.

In one example, such a method further comprises, subsequent to the sealing stage, and when the comparison signal is indicative of the measured impedance level being greater than or equal to the predetermined reference impedance level a completion stage comprising controlling the radio frequency signal generator to apply a radio frequency signal at a predetermined completion voltage level, lower than the predetermined sealing voltage level, for a predetermined completion time period; and ending supply of such radio frequency signals.

In one example, such a method further comprises measuring electrical current supplied to the first and second electrodes to generate a measured current signal, and detecting a short circuit between the first and second electrodes if the measured current signal indicates electrical current supplied to the first and second electrodes exceeds a first predetermined value for at least a predetermined time period.

DETAILED DESCRIPTION OF THE PREFERRED EMBODIMENTS

Figure 1:
FIGS. 1 and 2 show side views of a bipolar surgical instrument embodying one aspect of the present invention in open and closed positions respectively.
Figure 2:
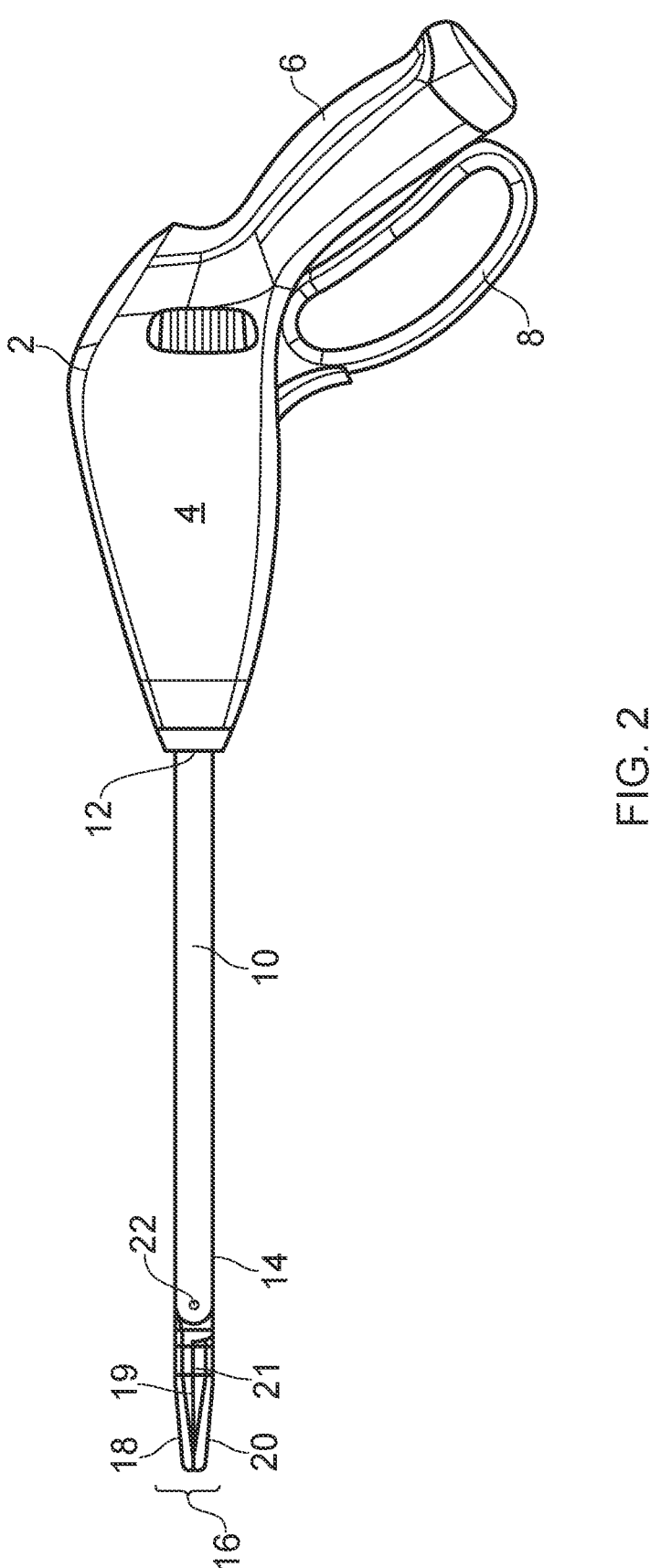

An example bipolar surgical instrument 1 is shown schematically in FIGS. 1 and 2. FIG. 1 illustrates an open position of the instrument 1, and FIG. 2 illustrates a closed position thereof.

The instrument 1 comprises a body 2 having a main housing 4 from which a fixed grip 6 extends. The fixed grip 6 is held during use by the operator of the instrument 1. A movable actuation grip 8 is movably mounted on the main housing 4 of the body 2. An elongate shaft 10 is attached to the main housing 4 of the body 2 and extends from a proximal end 12 at the main housing 4, to a distal end 14 of the shaft 10. The shaft 10 defines a longitudinal axis therealong, and an elongate passage extends from the proximal end 12 to the distal end 14 of the shaft 10.

A pair 16 of opposed jaws are located at the distal end 14 of the shaft 10. The pair 16 of jaws comprises a first jaw 18 and a second jaw 20. In the example of FIGS. 1 and 2, the first and second jaws 18 and 20 are pivotally mounted on a jaw pivot 22. The first and second jaws 18 and 20 are pivotable about the jaw pivot 22, between an open position (as shown in FIG. 1) in which the jaws 18 and 20 are separated from one another, and a closed position (as shown in FIG. 2) in which the jaws 18 and 20 are adjacent one another. In another example of a bipolar instrument embodying the present invention, only one of the jaws is movable. In another example, the movable jaw or jaws may be movable in any suitable manner, for example linearly, or in a combination of rotation and linear movement. The exact nature of the movement of the jaws is not important in the context of the present invention.

The first and second jaws 18 and 20 carry first and second electrodes 19 and 21 respectively. The first and second electrodes 19 and 21 are arranged to apply radio frequency electromagnetic energy to vessel held between the first and second jaws 18 and 20.

In use, the operator of the instrument 1 moves the actuation grip 8 from a first position (shown in FIG. 1) to a second position (shown in FIG. 2) in order to move the jaws 18 and 20 from the open position to the closed position. During an operation, vessel to be sealed is held between the jaws 18 and 20 in the closed position for a predetermined time period, with pressure applied by the operator, and with radio frequency energy applied to the vessel. The radio frequency energy serves to seal the held vessel.

Figure 3:
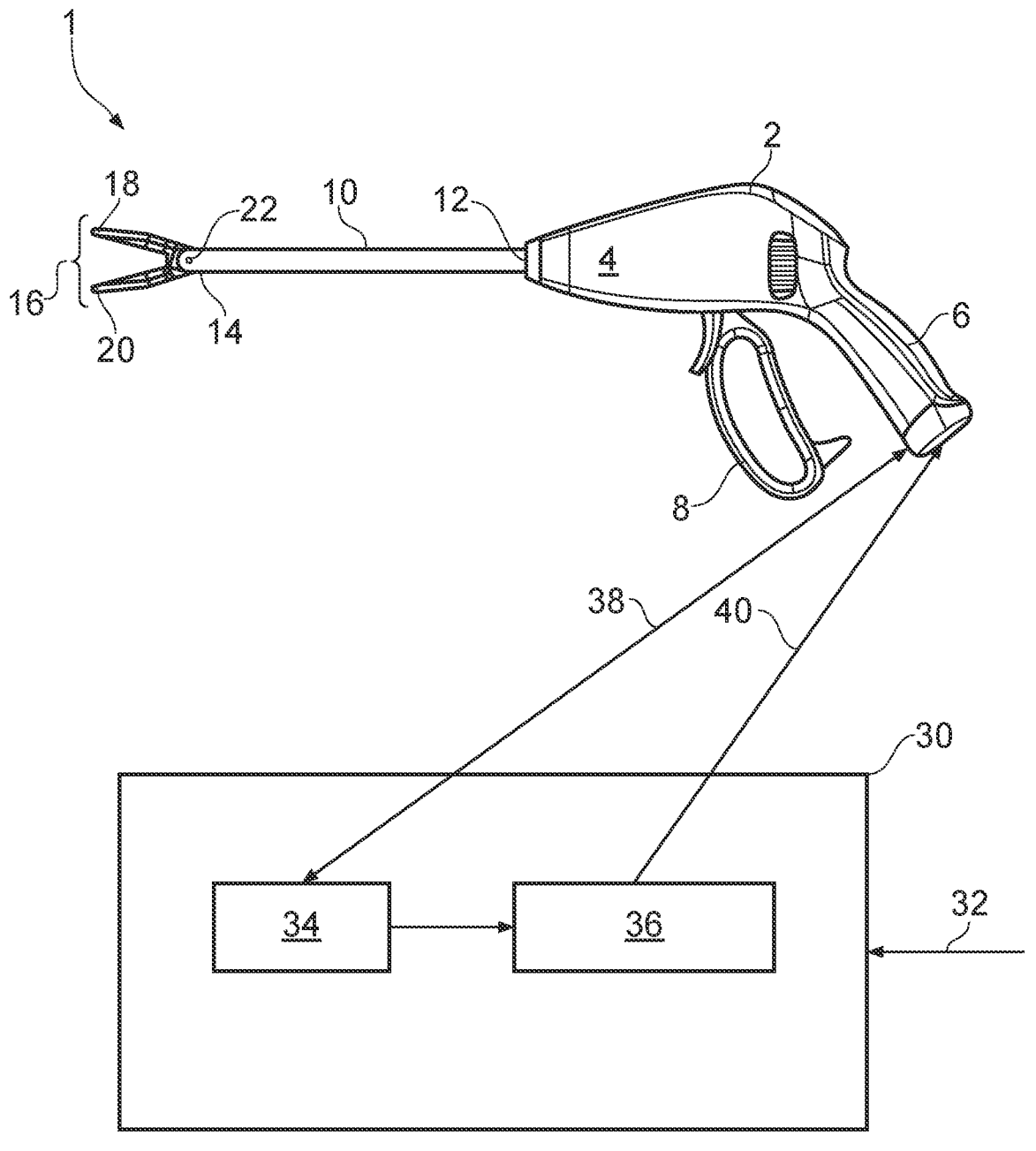
FIG. 3 illustrates a controller for use with a bipolar surgical instrument.

FIG. 3 illustrates the instrument 1 connected with a waveform generator 30. The waveform generator 30 receives an electrical power supply 32 and includes a controller 34 and a radio frequency signal generator 36. A control cable 38 connects the controller 34 to control inputs located, in one example, in or on the instrument 1. The control inputs may be located separately from the instrument 1, for example as a foot switch. A measurement cable may also be provided to provide a path for measurement signals.

The controller 34 is operable to control the signal generator 36 which is connected by power cable 40 to the instrument 1. The power cable 40 includes a pair of conductors that are connected to respective ones of the first and second electrodes 19 and 21 of the instrument 1. Upon reception of an appropriate control signal, for example from an operating switch such as a foot pedal, the controller 34 causes the signal generator 36 to supply a radio frequency electrical output signal via the power cable 40 to the first and second electrodes 19 and 21. One of the electrodes is defined as the active electrode and one as the return electrode.

The output radio frequency electrical signal in a system embodying the principles of present invention applies a desired sealing waveform to the vessel being held between the first and second jaws 18 and 20, which will be described below.

Figure 4:
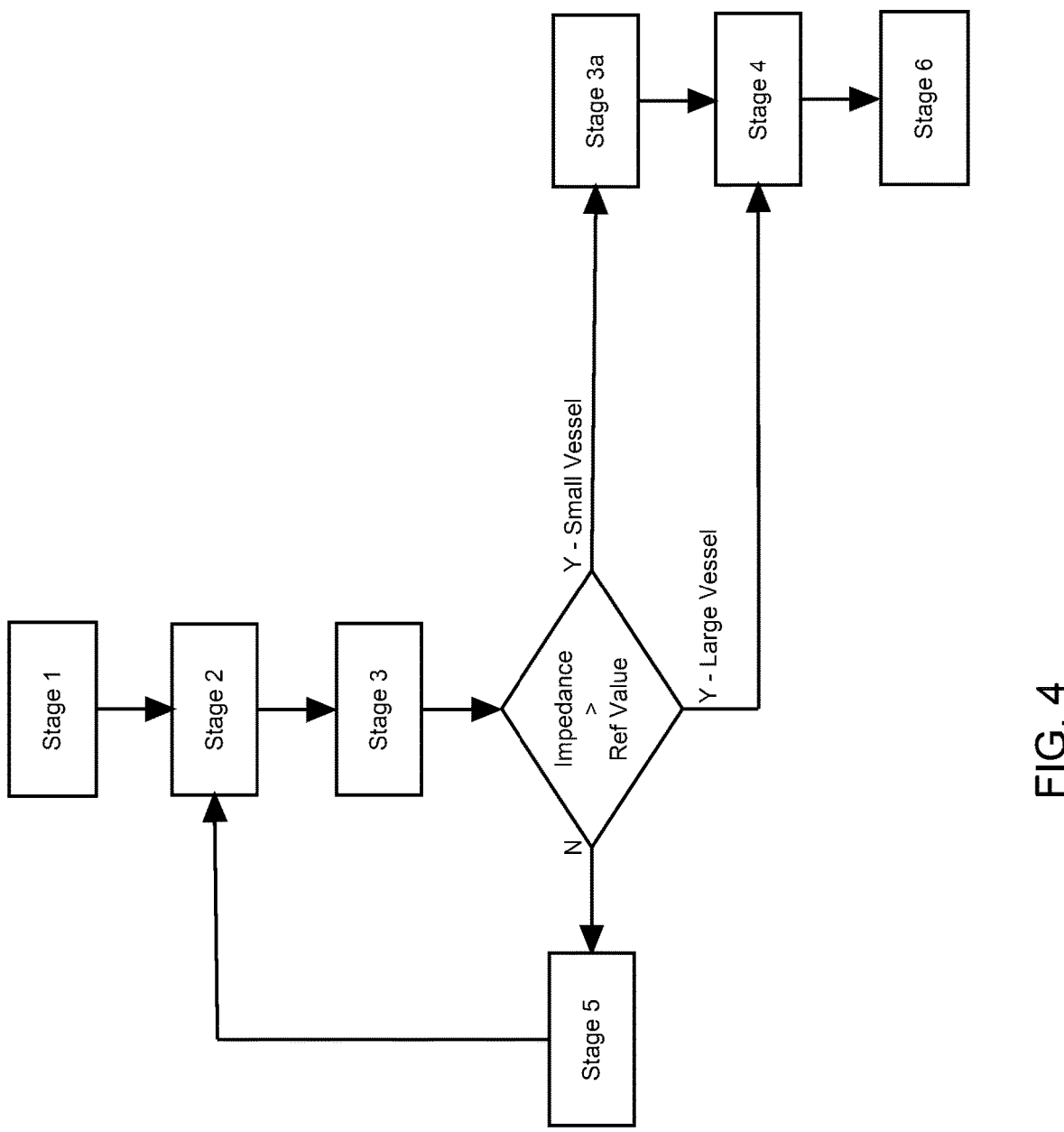
FIG. 4 is a flowchart illustrating steps in a method embodying another aspect of the present invention.
Figure 5:
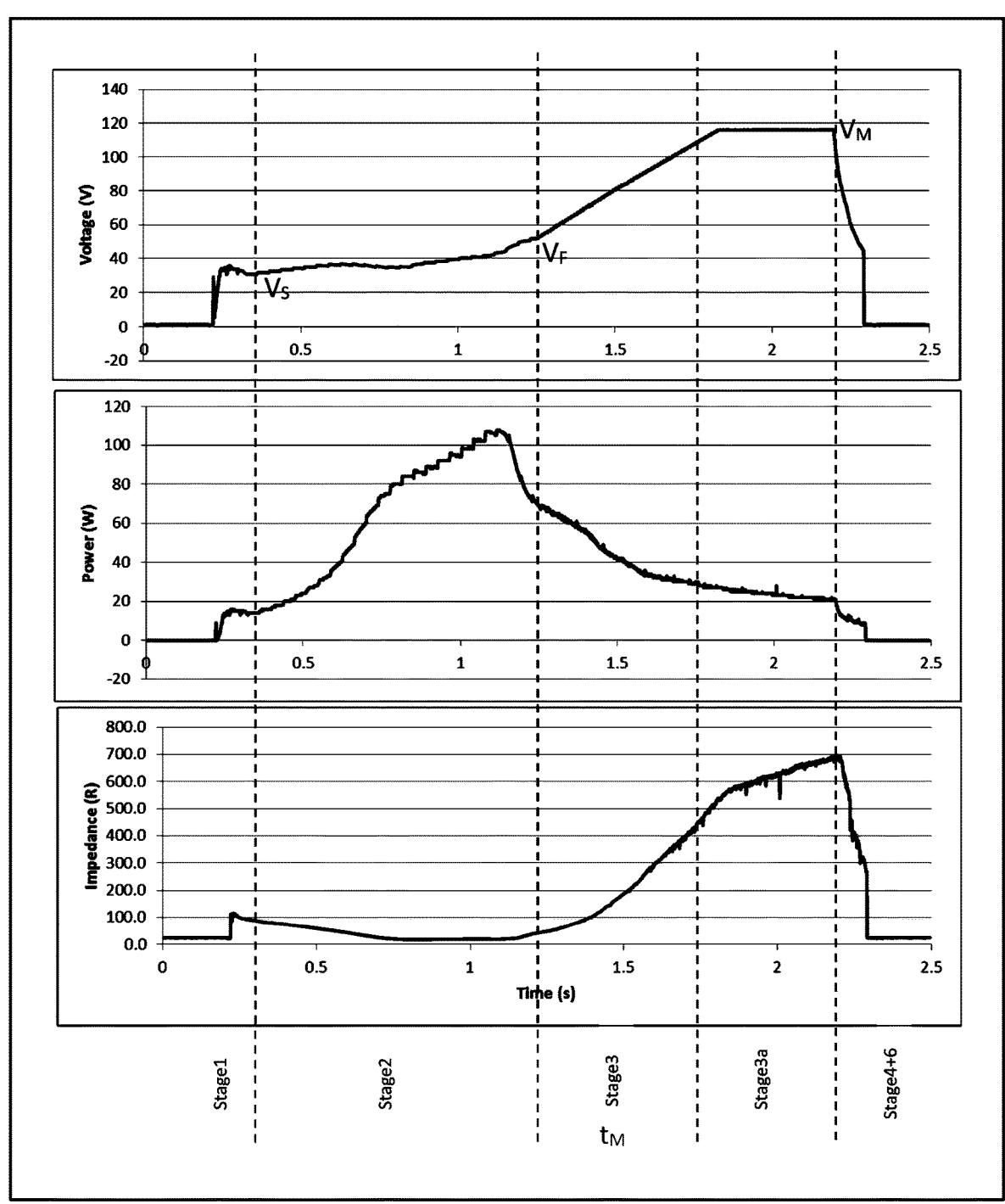
FIGS. 5 and 6 show graphs illustrating voltage, current, power and impedance against time for a bipolar surgical instrument operated in accordance with the method of FIG. 4.
Figure 6:
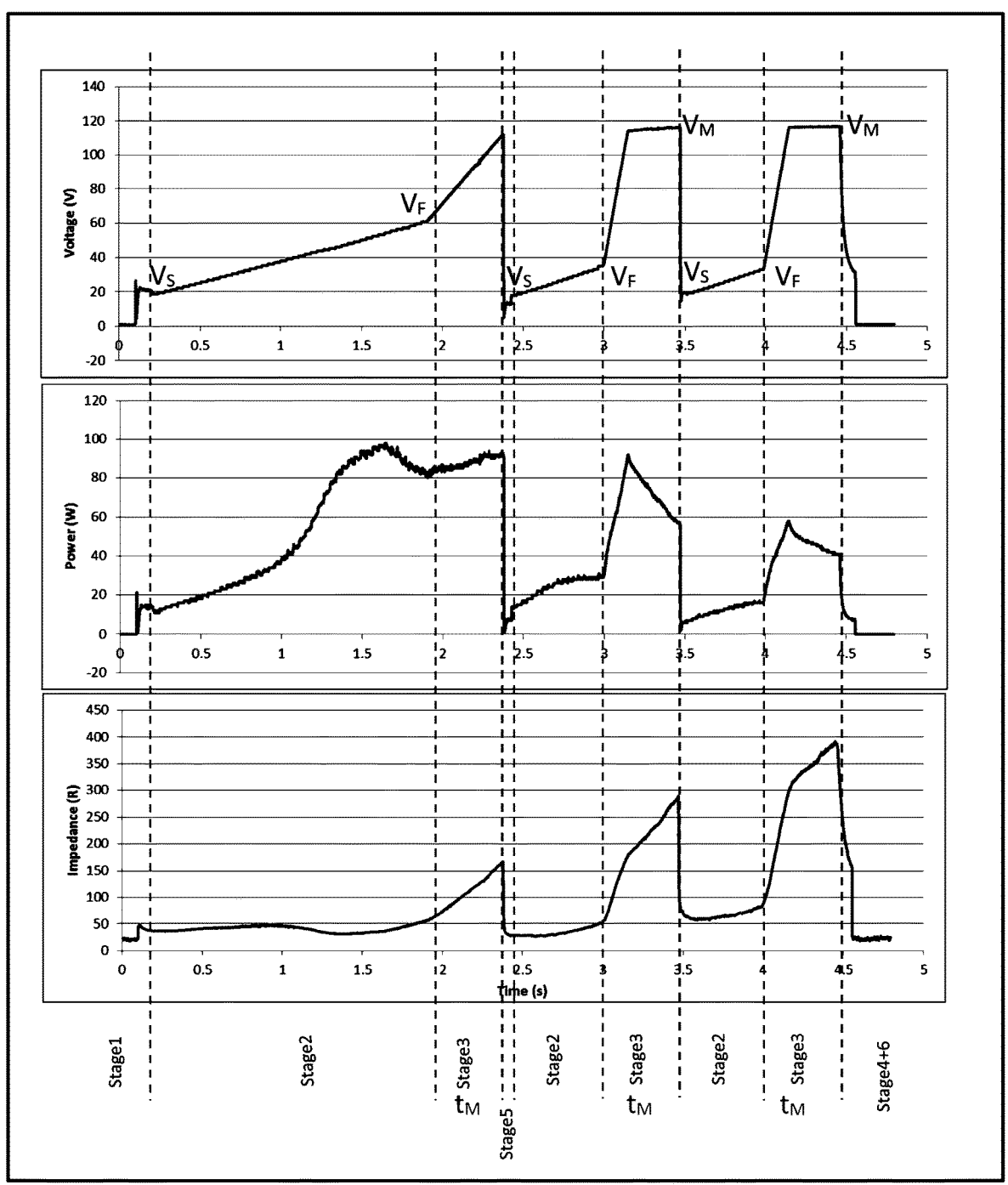

A method embodying one aspect of the present invention will now be described with reference to the flowchart of FIG. 4, and the graphs of FIGS. 5 and 6. The graphs of FIGS. 5 and 6 show exemplary voltage and power of the applied radio frequency signal, and exemplary measured impedance across the first and second electrodes of the surgical instrument 1.

In an embodiment of the present invention, stage 1 of the application of the radio frequency energy is an initial low-power stage, in which an appropriate starting voltage is determined. In stage 1, a constant power is applied to the vessel for a period of time short enough not to alter substantially the characteristics of the vessel. The constant power level may be in the range of up to 20 W, and may be applied for up to 200 ms. After the time period of application of the constant power level, the voltage required to maintain the initial power level is measured and is then used as the starting voltage $V_S$ for the vessel heating and sealing process.

Stage 2 applies a slow-ramping voltage across the first and second electrodes, which ramps up from the starting voltage determined in stage 1. Preferably, the applied voltage ramps in a linear manner. In one example, the voltage is ramped up from the starting voltage $V_S$ in discrete steps every millisecond. In one example, the voltage ramp rate is 0.02V/ms.

In order to determine when the boiling point of the vessel has been reached, without the need for a direct temperature measurement, the impedance of the vessel held between the jaws is measured. As pressure is applied to the vessel between the jaws, and the applied voltage increases, initially the impedance of the vessel drops. After an undefined time period, the vessel starts to coagulate, and the impedance increases from a minimum value.

In stage 2 of the present process, impedance is measured effectively continually, for example every 1 ms, as the applied voltage is ramped up. Each new impedance measurement is compared with a stored minimum impedance measurement for stage 2, and, if the new impedance measurement is lower than that previous impedance measurement, the new impedance measurement is stored as the minimum impedance measurement for stage 2. The impedance measurements continue during stage 2 until stage 2 is complete. The stored minimum impedance measurement at the end of stage 2 is then considered to be the minimum impedance level for stage 2 of the process.

Stage 2 is considered to be completed when the new impedance measurement is greater than the stored minimum impedance measurement by a predetermined value. For example, the predetermined value may be an absolute value of impedance, for example 20 R, or may be a proportion of the minimum impedance vale, such as 10%. When the initial stage 2 of the process is completed, then stage 3 commences.

Stage 3 of the process is a sealing and size detection process and takes place over a fixed hold time period $t_M$, for example 500 ms. During stage 3, the applied voltage is ramped-up from the final voltage $V_F$ applied at the end of stage 2, at a rate faster than that used during stage 2, towards a maximum voltage $V_M$, for example 115V. The applied voltage at the end of the stage 3 may not have reached the maximum voltage $V_M$, for example if $V_F$ is lower than expected, and the rate of increase of the applied voltage is not high enough to reach $V_M$. At the end of the hold time period, the impedance of the vessel is measured.

If the impedance is greater than a predetermined value, for example 200 R, 400 R or greater, then the vessel size is determined to be small, and the applied voltage is ramped up to the maximum level $V_M$ or held at the maximum level $V_M$ for an additional hold-time, for example 500 ms, in stage 3a.

For such small vessel sizes the process moves to stage 4, which is a seal-completed check. Initial stage 4 impedance is measured, and applied power is reduced to a predetermined low power level $P_L$, for example 5 W, for a predetermined check time $t_C$, for example 100 ms. The impedance is then measured. If the measured impedance value is lower than the initial stage 4 impedance, then the seal is determined as being made correctly, and the process moves to stage 6. If the measured impedance is greater than the initial stage 4 impedance, then the seal is determined to be incomplete, and an error generated before the process moves to stage 6. The resulting waveform for smaller vessels is shown in FIG. 5.

For larger vessel sizes, as determined by an impedance less than a predetermined value, for example up to 400 R at the end of stage 3, a re-ramping sequence is commenced by moving the process to stage 5. In stage 5, applied power is reduced, for example to 5 W, for a fixed period, for example 50 ms. Upon completion of this time period, the process repeats stages 2 and 3, in which the applied voltage is ramped up from the start voltage $V_S$. Stages 2 and 3 are repeated until the measured impedance is greater than or equal to a predetermined end-point impedance at the end of stage 3, for example 350 R. The process moves to stage 4, as for smaller vessels if the end point impedance is reached. The resulting waveform for larger vessels is shown in FIG. 6.

At stage 6, the radio frequency energy is terminated.

During the application process, the system monitors for open circuit faults, using the impedance measurements. If the impedance measurements are above a predetermined threshold value for a predetermined time period, an open-circuit condition is detected. For example, if the impedance is consistently above 1500 R for periods of 400 ms, then an open circuit is detected.

Similarly, during the application process, the system monitors for short circuit faults, using current measurements. If the current flow is greater than a predetermined threshold value for a predetermined time period, then a short-circuit condition is detected. The current threshold value is set to be higher than the current supplied during normal operating times. For example, if the current is consistently above 4.5 A RMS, for periods of 400 ms, then a short circuit is detected. Upon detection of a short circuit, the radio frequency power is shut off In such a manner, an embodiment of the present invention is able to provide improved vessel sealing characteristics for a bipolar electrosurgical instrument.

The invention claimed is:

1. An electrosurgical system comprising:
   a bipolar electrosurgical instrument comprising:
   a body;
   an elongate shaft (i) attached to the body and (ii) having
      a distal end;

first and second elongate jaw members at the distal end of the elongate shaft, the first elongate jaw member carrying a first electrode and the second elongate jaw member carrying a second electrode, the first and second elongate jaw members being movable relative to one another between an open position in which the first and second electrodes are spaced apart from one another and a closed position in which the first electrode is adjacent the second electrode; and a power cable having (i) a pair of electrically conductive elements, (ii) a first end for connection with a source of radio frequency electromagnetic energy, and (iii) a second end for connection to the first and second electrodes; and a waveform generator that is the source of radio frequency electromagnetic energy and comprising:

a radio frequency signal generator operable to supply a radio frequency signal to the first and second electrodes via the power cable; and a controller operable to control operation of the radio frequency signal generator, in dependence upon a received control input, wherein:

in a preheating stage, prior to a tissue heating stage, the controller is operable to:

control the radio frequency signal generator to supply the radio frequency signal of a predetermined initial power level of up to 20 Watts to the first and second electrodes for a predetermined initial time period of up to 200 milliseconds, such that characteristics of a target vessel are not substantially altered, the predetermined time period having an end time;

measure a voltage level between the first and second electrodes at the end time to determine a starting voltage to be used at a heating start time; and in the tissue heating stage after the preheating stage and before a tissue sealing stage, the controller is operable to:

control the radio frequency signal generator to supply the radio frequency signal at a controlled voltage level to the first and second electrodes, the controlled voltage level starting at the starting voltage, at the heating start time, then increasing the controlled voltage level to a final voltage at a heating end time;

measure an impedance between the first and second electrodes during the supply of the controlled voltage level;

detect a minimum measured impedance between the first and second electrodes during the supply of the controlled voltage; and declare the heating end time when a measured impedance is greater than the minimum measured impedance by a first predetermined amount.

2. The electrosurgical system according to claim 1, wherein the controller is operable to increase the controlled voltage level linearly between the starting voltage and the heating end time voltage.

3. The electrosurgical system according to claim 1, wherein:

in the tissue sealing stage, the controller is operable to:

increase the controlled voltage level linearly from the heating end time voltage to a predetermined sealing voltage level applied at a constant level for a predetermined sealing time period having a sealing end time, a rate of the controlled voltage level increase during the tissue sealing stage being larger than a rate of the controlled voltage increase during the tissue heating stage;

measure an impedance level between the first and second electrodes at the sealing end time;

compare a measured sealing impedance at the sealing end time with a predetermined reference impedance; and declare the sealing end time to end the tissue sealing stage when the measured sealing impedance is greater than or equal to the predetermined reference impedance.

4. The electrosurgical system according to claim 3, wherein the controller is operable such that, in response to the measured sealing impedance at the sealing end time being greater than a predetermined value, the controlled voltage level is held at a maximum voltage level for a predetermined hold time.

5. The electrosurgical system according to claim 1, wherein the first predetermined amount is a predetermined portion of a minimum value of the measured impedance.

6. An electrosurgical system comprising:

a bipolar electrosurgical instrument comprising:

a body;

an elongate shaft (i) attached to the body and (ii) having a distal end;

first and second elongate jaw members at the distal end of the elongate shaft, the first elongate jaw member carrying a first electrode and the second elongate jaw member carrying a second electrode, the first and second elongate jaw members being movable relative to one another between an open position in which the first and second electrodes are spaced apart from one another and a closed position in which the first electrode is adjacent the second electrode; and a power cable having (i) a pair of electrically conductive elements, (ii) a first end for connection with a source of radio frequency electromagnetic energy, and (iii) a second end for connection to the first and second electrodes; and a waveform generator that is the source of radio frequency electromagnetic energy and comprising:

a radio frequency signal generator operable to supply a radio frequency signal to the first and second electrodes via the power cable; and a controller operable to control operation of the radio frequency signal generator, in dependence upon a received control input, wherein:

in a preheating stage, prior to a tissue heating stage, the controller is operable to:

control the radio frequency signal generator to supply the radio frequency signal of a predetermined initial power level of up to 20 Watts to the first and second electrodes for a predetermined initial time period of up to 200 milliseconds, such that characteristics of a target vessel are not substantially altered, the predetermined time period having an end time;

measure a voltage level between the first and second electrodes at the end time to determine a starting voltage to be used at a heating start time for the tissue heating stage; and in the tissue heating stage after the preheating stage and before a tissue sealing stage, the controller is operable to:

control the radio frequency signal generator to supply the radio frequency signal at a controlled voltage level to the first and second electrodes, the controlled voltage level starting at the starting voltage, at the heating start time, then increasing the controlled voltage level to a heating end time voltage level at a heating end time;

measure an impedance between the first and second electrodes during the supply of the controlled voltage level; and in response to the measured impedance at the heating end time being greater than a predetermined value, holding the controlled voltage level at a maximum value of the controlled voltage level for a predetermined hold time.

7. An electrosurgical system comprising:

a bipolar electrosurgical instrument comprising:

a body;

an elongate shaft (i) attached to the body and (ii) having a distal end;

first and second elongate jaw members at the distal end of the elongate shaft, the first elongate jaw member carrying a first electrode and the second elongate jaw member carrying a second electrode, the first and second elongate jaw members being movable relative to one another between an open position in which the first and second electrodes are spaced apart from one another and a closed position in which the first electrode is adjacent the second electrode; and a power cable having (i) a pair of electrically conductive elements, (ii) a first end for connection with a source of radio frequency electromagnetic energy, and (iii) a second end for connection to the first and second electrodes; and a waveform generator that is the source of radio frequency electromagnetic energy and comprising:

a radio frequency signal generator operable to supply a radio frequency signal to the first and second electrodes via the power cable; and a controller operable to control operation of the radio frequency signal generator, in dependence upon a received control input, wherein, in a tissue heating stage after a preheating stage and prior to a tissue sealing stage, the controller is operable to:

control the radio frequency signal generator to supply the radio frequency signal at a controlled voltage level to the first and second electrodes, the controlled voltage level starting at a starting voltage at a heating start time, increasing during the heating stage to a heating stage final voltage at a heating end time;

measure an impedance between the first and second electrodes during the supply of the controlled voltage level;

detect a minimum measured impedance between the first and second electrodes during the supply of the controlled voltage; and declare the heating end time when a measured impedance is greater than the minimum measured impedance by a first predetermined amount; and in the tissue sealing stage, the controller is operable to:

supply the radio frequency signal at a constant predetermined sealing voltage level to the first and second electrodes for a predetermined sealing time period having a sealing end time, the constant predetermined sealing voltage level being greater than the heating stage final voltage;

measure an impedance level between the first and second electrodes at the sealing end time;

compare a measured sealing impedance at the sealing end time with a predetermined reference value;

in response to the measured sealing impedance at the sealing end time being greater than the predetermined value, holding the controlled voltage level at a maximum voltage level for a predetermined hold time;

after the predetermined hold time, measure a post-hold sealing impedance;

reducing a power associated with the controlled voltage level and then measuring the impedance level again; and in response to the sealing impedance measured after reducing the power being lower than the post-hold sealing impedance, terminate the radio frequency energy.

8. The electrosurgical system according to claim 7, wherein, after the tissue heating stage, in response to the measured impedance being less than the minimum measured impedance by the first predetermined amount, the controller is operable to:

repeat the tissue heating and tissue sealing stages until the measured impedance is greater than the minimum measured impedance by at least the first predetermined amount; and supply the radio frequency signal at the starting voltage and increasing to the heating stage final voltage at each heating end time each time the tissue heating stage is repeated; and increasing the heating stage final voltage linearly to the predetermined sealing voltage level each time the tissue sealing stage is repeated.

* * * * *